(12) United States Patent
Crawford et al.

(10) Patent No.: US 8,431,745 B2
(45) Date of Patent: Apr. 30, 2013

(54) PROCESS FOR PREPARATION OF HIV PROTEASE INHIBITORS

(75) Inventors: Kenneth R. Crawford, Westwood, MA (US); Eric D. Dowdy, Foster City, CA (US); Arnold Gutierrez, San Jose, CA (US); Richard P. Polniaszek, Half Moon Bay, CA (US); Richard Hung Chiu Yu, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/401,659

(22) Filed: Feb. 21, 2012

(65) Prior Publication Data

US 2012/0258935 A1    Oct. 11, 2012

Related U.S. Application Data

(62) Division of application No. 11/729,522, filed on Mar. 29, 2007, now Pat. No. 8,173,623.

(60) Provisional application No. 60/787,126, filed on Mar. 29, 2006.

(51) Int. Cl.
*C07C 381/00*    (2006.01)

(52) U.S. Cl.
USPC .......................................................... 564/89

(58) Field of Classification Search ..................... 564/89
See application file for complete search history.

*Primary Examiner* — John Mabry

(57) ABSTRACT

A process for the synthesis of bisfuran intermediates useful for preparing antiviral HIV protease inhibitor compounds is hereby disclosed.

3 Claims, 1 Drawing Sheet

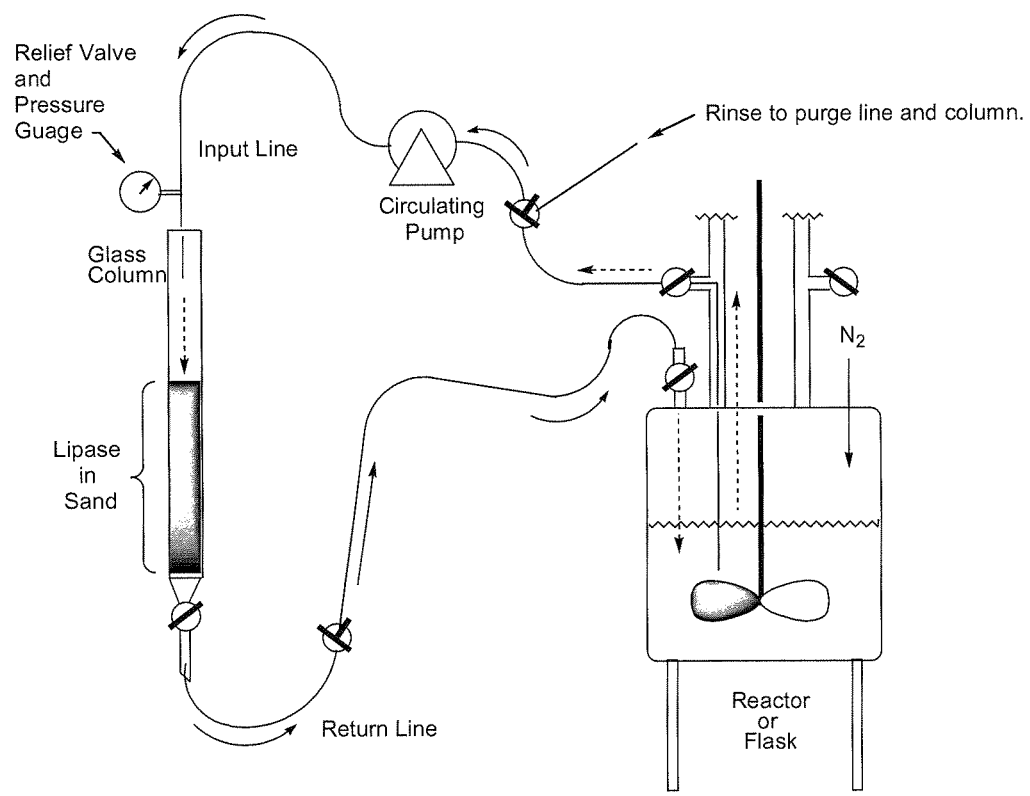

PROCESS FOR PREPARATION OF HIV PROTEASE INHIBITORS

CROSS-REFERENCE TO RELATED APPLICATION

This application is a division of U.S. patent application Ser. No. 11/729,522, filed on Mar. 29, 2007 now U.S. Pat. No. 8,173,623, which claims priority to U.S. Provisional Patent Application No. 60/787,126, filed Mar. 29, 2006.

FIELD OF THE INVENTION

The invention relates generally to processes for the preparation of antiviral compounds with anti-HIV protease properties. The invention relates to the methods for the preparation of carbamate sulfonamide amino phosphonate esters and intermediates thereof. The invention also relates to the novel intermediates prepared by these methods. The carbamate sulfonamide amino phosphonate esters prepared by the present methods are HIV protease inhibitors, useful for the treatment of human auto immunodeficiency syndrome (AIDS).

BACKGROUND OF THE INVENTION

IDS is a major public health problem worldwide. Although drugs targeting HIV viruses are in wide use and have shown effectiveness, toxicity and development of resistant strains have limited their usefulness. Assay methods capable of determining the presence, absence or amounts of HIV viruses are of practical utility in the search for inhibitors as well as for diagnosing the presence of HIV.

A conventional process for preparation of a HIV protease inhibitor (PI) of Formula I

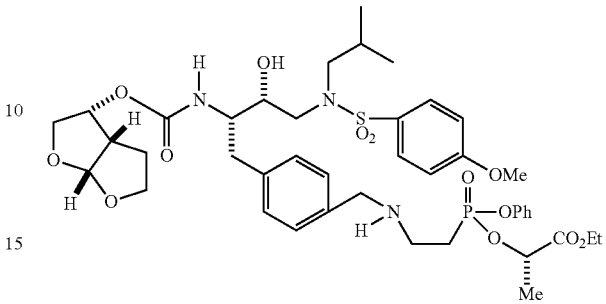

Formula I is lengthy, affords a low yield of approximately 1%, is variably reproducible, requiring numerous chromatographic purification steps, and employs undesirable reagents, such as ozone, sodium cyanoborohydride, and tributyltin hydride. The compound of Formula I is an HIV protease inhibitor which has been made and disclosed in WO2003/090690.

Methods for the preparation of the bisfuran alcohol intermediate used in the synthesis of the compound of formula I have been described by Pezechk (Pezechk, M. et al., Tetrahedron Letters, 1986, 27, 3715.) and Ghosh (Ghosh, A. K. et al., J. Med. Chem., 1994, 37, 2506; Ghosh A. K. et al., J. Med. Chem., 1996, 39, 3278; Ghosh, A. K. et al., Tetrahedron Letters, 1995, 36, 505).

Scheme 1 shows the bisfuran alcohol synthesis from Ghosh, A. K. et al., Tetrahedron Letters, 1995, 36, 505).

Scheme 1

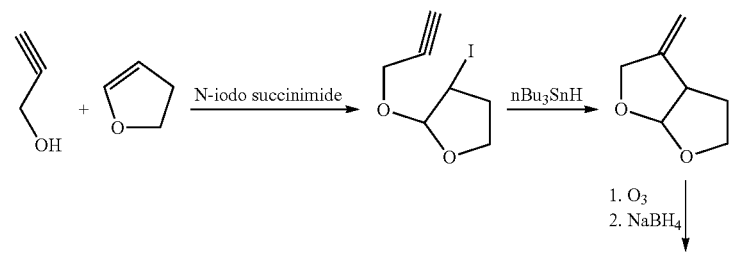

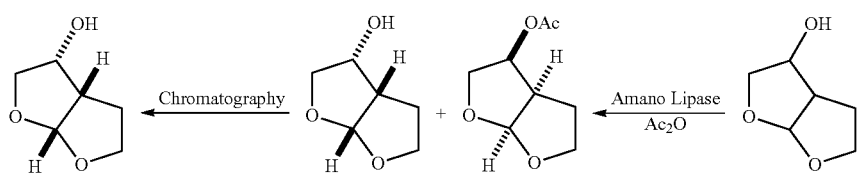

Conventional methods require multiple steps and the use of toxic reagents. In one of the methods (Ghosh, A. K. et al., Tetrahedron Letters, 1995, 36, 505), resolution of a racemic mixture was achieved by exposure to an immobilized enzyme followed by chromatographic separation.

Reactive carbonate esters have been prepared from bisfuran alcohol (1) and dipyridyl carbonate (Ghosh A. K. et al., J. Med. Chem., 1996, 39, 3278), and p-nitrophenol chloroformate (X. Chen et al., Bioorganic and Medicinal Chemistry Letters, 1996, 6, 2847). These reagents couple with nucleophilic reaction partners, but do not always display the appropriate reactivity and efficiency.

Methods exist for the preparation of chiral haloalcohols derived from N=protected amino acids (Albeck, A. et al., Tetrahedron, 1994, 50, 6333). Methods for the conversion of such chloroalcohols to carbamate sulfonamide derivatives are known (Malik, A. et al., WO 01/46120A1). The halohydrins can also be converted to epoxides and converted to carbamate sulfonamide derivatives in a similar manner (WO 03/090690).

Preparation of carbamate derivatives of aminophosphonic acids and subsequent conversion to phosphonate mono- and diesters have been described in Yamauchi, K. et al., J. Org. Chem., 1984, 49, 1158; Yamauchi, K. et al., J. Chem. Soc. Perkin Trans. I, 1986, 765.

Aminoethyl phosphonate diesters can be prepared by a process involving acylation of an amino phosphonic acid with acyl halides or benzyl chloroformate (CBZCl) to form compounds of Formula VII Formula VII Compounds of Formula VII can be activated and condensed with phenol to form a compound of Formula VIII Formula VIII A compound of Formula VIII can be activated and condensed with a second alcohol or phenol to form IX Formula IX A compound of Formula IX can be deacylated to form an amino phosphonate compound of Formula X Formula X A compound of Formula X can be isolated as a salt of an organic or inorganic acid.

The Ghosh process for bisfuran alcohol (Ghosh, A. K. et al, J. Org. Chem., 1995, 36, 505) requires the use of tributyltin hydride and ozone.

The free base of a compound of Formula I is non-crystalline and hygroscopic with limited stability in protic solvents.

Thus, there exists a need to develop syntheses of more stable forms of the PI of Formula I. There also exists a need to develop more efficient processes of synthesizing the PI of Formula I.

SUMMARY OF THE INVENTION

The present invention provides improved methods to bisfuran alcohol derivatives, amino phoshonate derivatives and a process to prepare carbamate sulfonamide aminoethyl phosphonate diesters useful for the treatment of human auto immunodeficiency syndrome (AIDS).

In one embodiment, the invention provides a process for the preparation of a bisfuran alcohol of Formula 0:

Formula 0 comprising
reacting 2,3-dihydrofuran and glycoaldehyde or glycoaldehyde dimer in the presence of a lanthanide or transition metal catalyst to form the bisfuran alcohol of Formula 0.

BRIEF DESCRIPTION OF THE DRAWINGS

FIG. 1 illustrates a column method for the enantiomeric resolution of (3R,3aS,6aR)hexahydrofuro[2,3-b]furan-3-ol, (1) as shown in the examples.

DETAILED DESCRIPTION OF EXEMPLARY EMBODIMENTS

Definitions

Unless stated otherwise, the following terms and phrases as used herein are intended to have the following meanings:

When tradenames are used herein, applicants intend to independently include the tradename product and the active pharmaceutical ingredient(s) of the tradename product.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

"Lanthanides" refers to the following elements and their ions: La, Ce, Pr, Nd, Pm, Sm, Eu, Gd, Tb, Dy, Ho, Er, Tm, Yb, Lu.

"Transition metals" refer to the following elements and their ions: Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg.

Ligands comprising the metal catalysts may be chiral, achiral or racemic.

SCHEMES AND EXAMPLES

General aspects of these exemplary methods are described below and in the Examples. Each of the products of the following processes is optionally separated, isolated, and/or purified prior to its use in subsequent processes.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

EXEMPLARY EMBODIMENTS

In one embodiment, the invention provides a compound of Formula C and a pharmaceutically acceptable salt thereof:

Formula C

In another embodiment, the invention provides a process of preparing a compound of Formula M comprising a) treating a compound of Formula E with an amine such as 1-amino-2-methylpropane Formula E to form a compound of Formula F Formula F b) treating the compound of Formula F with a compound of Formula G Formula G to form a compound of Formula C Formula C c) treating the compound of Formula C with a reducing agent to form the compound of Formula M Formula M Typical reducing agent which can be used to effect the transformation of the nitrile moiety to the carboxaldehyde moiety can found in Larock, Richard, C. "Comprehensive Organic Transformations 2$^{nd}$ Ed. 1999 John Wiley and Sons publisher, pages 1271-1272.

In another embodiment, the invention provides a compound of Formula M:

Formula M

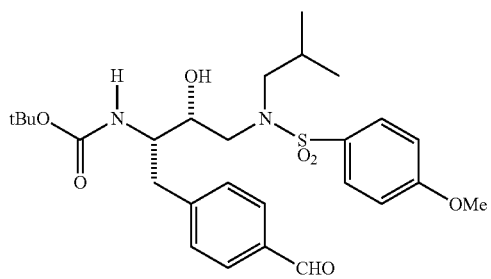

In another embodiment, the invention provides a process for the preparation of a compound of Formula M:

Formula M

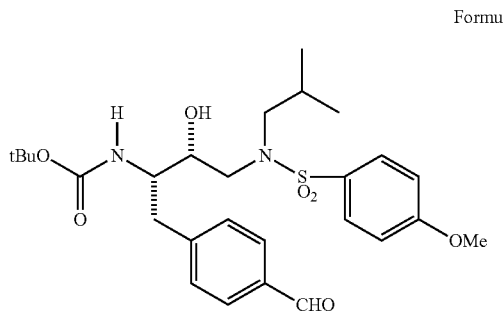

comprising
treating a compound of Formula C with a reducing agent to form the compound of Formula M Formula C

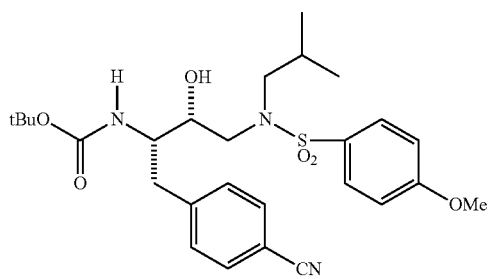

In another embodiment, the invention provides a process of preparing the compound of Formula M, wherein the reducing agent is diisobutyl aluminum hydride.

In another embodiment, the invention provides a process of preparing a compound of Formula 0, further comprising
treating the bisfuran alcohol of Formula 0 with disuccinimidyl dicarbonate to form a compound of Formula L1

Formula L1

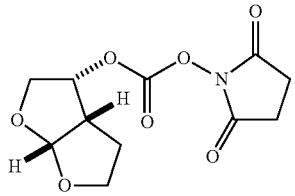

In another embodiment, the invention provides a process of preparing the compound of Formula 0, further comprising
treating the bisfuran alcohol of Formula 0 with bis(p-nitrophenyl) carbonate or p-nitrophenol chloroformate to form a compound of Formula L2

Formula L2

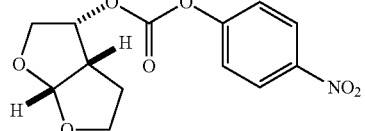

In another embodiment, the invention provides a process of preparing the compound of Formula 0, further comprising
treating the bisfuran alcohol of Formula 0 with dipyridyl carbonate to form a compound of Formula L3

Formula L3

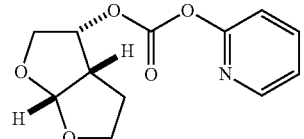

In another embodiment, the invention provides a compound and pharmaceutically acceptable salts thereof having Formula N Formula N

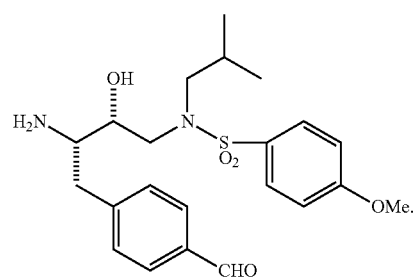

In another embodiment, the invention provides a compound and pharmaceutically acceptable salts thereof having Formula A Formula A

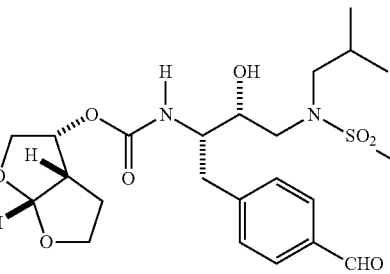

In another embodiment, the invention provides a process for the preparation of carbamate sulfonamide amino phosphonate esters which comprises:
a) addition of a dihydrofuran to a glycoaldehyde or glycoaldehyde dimer in the presence of a Yb, Pr, Cu, Eu or Sc catalyst to form the bisfuran alcohol of Formula 0

Formula 0

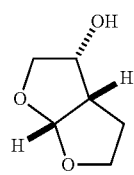

b) treating the reaction product of step (a) with disuccinimidyl dicarbonate, bis(p-nitro)phenyl carbonate, p-nitrophenol chloroformate, or dipyridyl carbonate to form a compound of Formula L1, Formula L2, Formula L2, or Formula L3, respectively, Formula L1

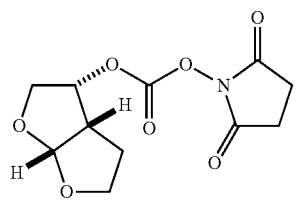

Formula L2

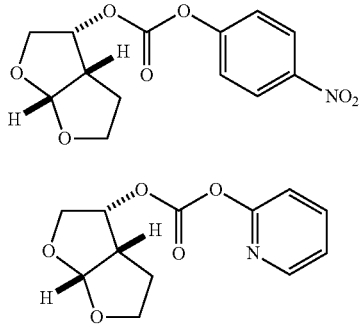

Formula L3

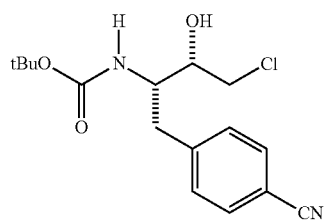

c) treating a compound of Formula E with an amine

Formula E

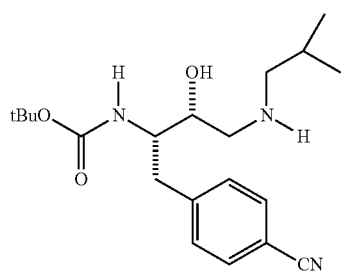

to form a compound of Formula F

Formula F d) treating a compound of Formula F with a compound of Formula G

Formula G

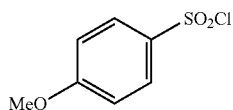

to form a compound of Formula C

Formula C

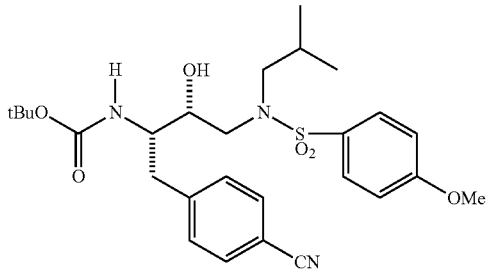

e) treating a compound of Formula C with a reducing agent to form a compound of Formula M Formula M

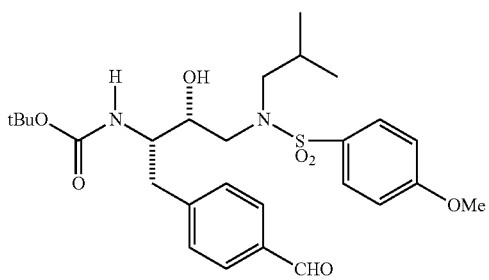

f) deprotecting a compound of Formula M with trifluoroacetic acid, hydrochloric acid, toluenesulfonic acid, methanesulfonic acid, benzenesulfonic acid, hydrobromic acid or another suitable acid as listed in *Protective Groups in Organic Chemistry*, Theodora W. Greene, John Wiley & Sons, Inc., New York, 1991, to form a compound of Formula N Formula N

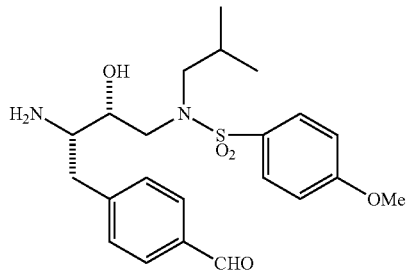

g) treating a compound of Formula N with a compound of Formula L, L2, or L3 to form a compound of Formula A h) treating a compound of Formula A with a compound of Formula J

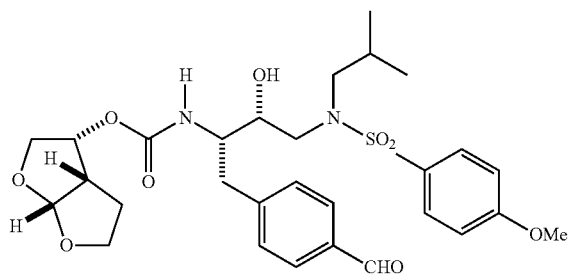
Formula A

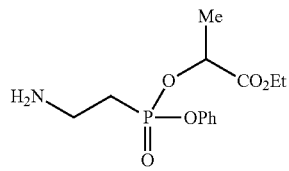
Formula J to form a compound of Formula I

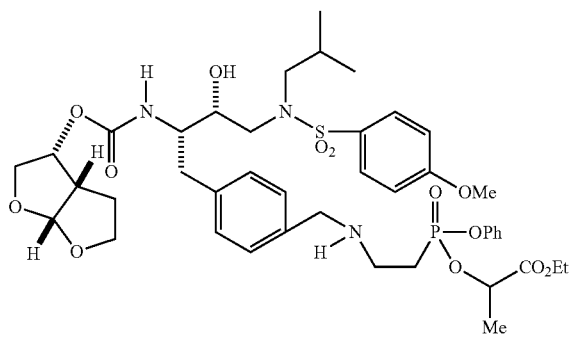
Formula I i) treating a compound of Formula I with adipic acid to form a salt of formula IV

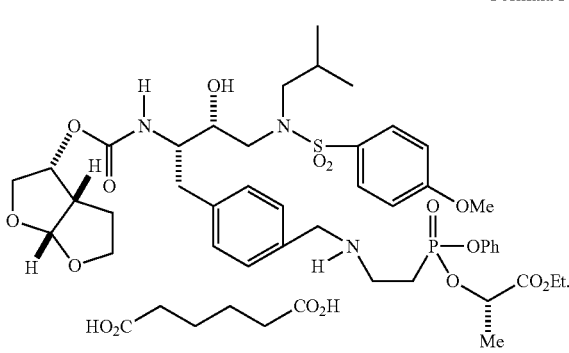
Formula IV

In another embodiment, the invention provides a salt having Formula IV:

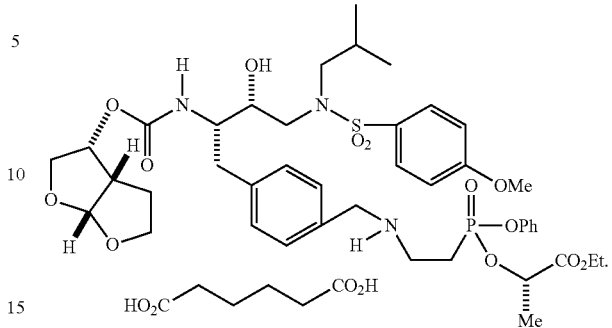
Formula IV

The salt of formula IV was prepared and has a melting point of 118° C.-121° C. The free base of the salt of formula IV is an HIV protease inhibitor which has been made and disclosed in WO2003/090690, which is herein incorporated by reference. The salt of Formula IV is also an HIV protease inhibitor useful for treating patients infected by HIV.

TABLE 1

Chiral catalysts in bisfuran alcohol formation.

| Entry | Conditions | Catalyst | Solvent | Conversion (%) | GC Analysis[1] [(−)-1 to (+)-1] |
|---|---|---|---|---|---|
| 1 | 50° C., 5 hr | Yb(hfc)$_3$ (+) | DHF | 100 | 49 to 51 |
| 2 | 50° C., 5 hr | Yb(hfc)$_3$ (−) | DHF | 100 | 50 to 50 |
| 3 | 50° C., 5 hr | Eu(hfc)$_3$ (+) | DHF | 100 | 48 to 52 |
| 4 | r.t., 20 hr | Yb(fod)$_3$, S-binaphthol | MTBE | 100 | 50 to 50 |
| 5 | 50° C., 5 hr | Yb(tfc)$_3$ (+) | DHF | 100 | 52 to 48 |
| 6 | 50° C., 5 hr | Pr(tfc)$_3$ (+) | DHF | 100 | 56 to 44 |
| 7 | 50° C., 2.5 hr | Yb[(R)-(−)-BNP]$_3$ | DHF | 100 | 60:40 |
| 8 | 30° C., 12 hr | Yb[(R)-(−)-BNP]$_3$ | DHF | 100 | 59:41 |
| 9 | 50° C., 5 hr | Yb[(R)-(−)-BNP]$_3$ | DHF | 100 | 65:35 |
| 10 | r.t., 5 hr | Cu[Pybox] | DHF | Polymerized | DNA |
| 11 | 50° C., 5 hr | Cu[Pybox] | DHF | Polymerized | DNA |
| 12 | r.t., 5 hr | Cu[Pybox] | DCM | <5 | DNA |
| 13 | 50° C., 5 hr | Cu[Pybox] | DCM | 0 | DNA |
| 14 | r.t., 20 hr | Cu[Pybox] | DHF/DCM | 0 | DNA |

DHF = dihydrofuran,
DCM = dichloromethane,
MTBE = methyl-t-butylether.

[1] GC analyses were performed by derivatizing bisfuran alcohol to the trifluoroacetate with trifluoroacetic anhydride in DCM.

TABLE 1-continued

Chiral catalysts in bisfuran alcohol formation.

M(hfc)₃ (−) = [structure of camphor-derived ligand with CF₃CF₂CF₂ group coordinated to M]₃

M(fod)₃ = [structure with CF₃CF₂CF₂ and (CH₃)₃C groups coordinated to M]₃

M(tfc)₃ (+) = [camphor-derived structure with CF₃ group coordinated to M]₃

CuPybox = [pyridine-bisoxazoline Cu complex with two Ph groups]²⁺ 2 SbF₆⁻

TABLE 2

Use of scandium (III) catalyst and chiral ligands to directly access (−)-1.

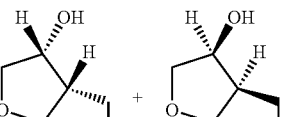

Sc(OTf)₃, ligand (S)-Pybox with Ph groups, Conditions → products (−)-1 and (+)-1

TABLE 2-continued

Use of scandium (III) catalyst and chiral ligands to directly access (−)-1.

(−)-1     (+)-1

| Entry | Catalyst Mol % | Ligand Mol % | Temp (° C.) | Time (hrs) | Solvent | Conversion (%) | GC Analysis[1] [(−) to (+)] |
|---|---|---|---|---|---|---|---|
| 1 | 3.4 | 7.5 | r.t. | (3)5 | DCM | 100 | 79:21 |
| 2 | 3.4 | 3.6 | −10 to r.t. | (3)5 | DCM | 100 | 62:38 |
| 3 | 20.0 | 21.4 | r.t. | (3)24 | DCM | <10 | NA |
| 4 | 3.4 | 7.6 | r.t. | (3)24 | DCM | <10 | NA |
| 5 | 3.4 | 7.5 | r.t. | (3)5 | DCM | 100 | 78:22 |
| 6 | 3.35 | 9.37 | 50 | (3)5 | DCM | <10 | NA |
| 7 | 3.35 | 9.37 | r.t. | (3)5 | THF | <10 | NA |
| 8 | 3.35 | 9.37 | r.t. | (3)5 | MTBE/DME | <10 | NA |
| 9 | 3.35 | 9.37 | 0 | (3)5 | THF | 100 | 75:25 |
| 10 | 3.35 | 9.37 | r.t. | (3)5 | MeCN | 100 | 74:26 |
| 11 | 6.7 | 18.74 | r.t. | (3)5 | DCM | 100 | 82:18 |
| 12 | 10.0 | 60.0 | r.t. | (3)5 | DCM | 100 | 82:18 |
| 13 | 6.7 | 18.74 | r.t. | (3)5 | TFT | <5 | NA |
| 14 | 6.7 | 18.74 | 0 | (3)5 | DCM | 100 | 85:15 |
| 15 | 6.7 | 18.74 | 0 | (3)6 | CHCl₃ | >10 | NA |
| 16 | 6.7 | 18.74 | −78 | (3)6 | DCM | 0 | NA |
| 17 | 6.7 | 18.74 | −20 | (3)6 | DCM | <5 | NA |
| 18 | 6.7 | 18.74 | 0 to −5 | (5)68 | DCM | 100 | 82:18 |

TFT = trifluorotoluene,
DME = dimethoxyethane,
DCM = dichloromethane,
MTBE = methyl-t-butylether,
THF = tetrahydrofuran.
[1]GC analyses were performed by derivatizing bisfuran alcohol to the trifluoroacetate with trifluoroacetic anhydride in DCM.

TABLE 3

Use of catalysts and chiral ligands to directly access (−)-1.

2 + 6 (Catalyst, Ligand, Conditions) → (−)-1 + (+)-1

| Entry | Catalyst Used | Catalyst Mol % | Ligand Used | Ligand Mol % | Temp (° C.) | Time (hrs) | Solvent | GC Analysis[1] [(−) to (+)] |
|---|---|---|---|---|---|---|---|---|
| 1 | Sc(OTf)₃ | 3.4 | 2 | 7.5 | r.t. | (3)24 | DCM | Messy |
| 2 | Sc(OTf)₃ | 3.4 | 2 | 7.5 | r.t. | (3)5 | DCM | 26:74 |
| 3 | Yb(OTf)₃ | 3.4 | 2 | 7.6 | r.t. | (3)3 | DCM | 50:50 |
| 4 | Sc(OTf)₃ | 3.4 | 2 | 12.0 | r.t. | (3)5 | DCM | 23:77 |
| 5 | Sc(OTf)₃ | 3.35 | 3 | 7.54 | r.t. | (3)5 | DCM | 51:49 |
| 6 | Sc(OTf)₃ | 3.5 | 4 | 7.5 | r.t. | (3)5 | DCM | 57:43 |
| 7 | Cu(OTf)₂ | 4.8 | 5 | 5.6 | r.t. | (0.5)3 | DCM | 52:48 |

TABLE 3-continued

Use of catalysts and chiral ligands to directly access (-)-1.

| 8 | Cu(OTf)$_2$ | 5.6 | 5 | 13.97 | r.t. | (3)5 | DCM | 52:48 |
| 9 | Yb(OTf)$_3$ | 6.7 | 1 | 18.74 | r.t. | (3)5 | DCM | 61:39 |

[1]GC analyses were performed by derivatizing bisfuran alcohol to the trifluoroacetate with trifluoroacetic anhydride in DCM.

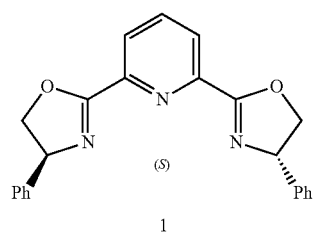

1

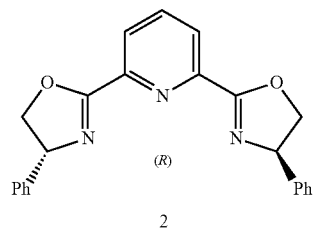

2

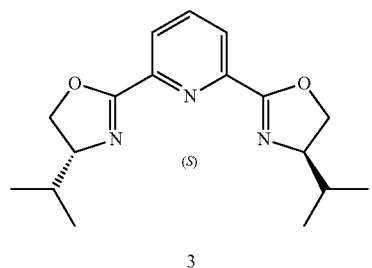

3

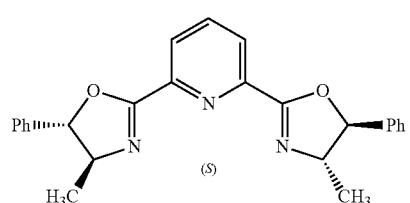

4

TABLE 3-continued

Use of catalysts and chiral ligands to directly access (-)-1.

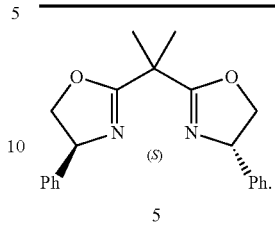

5

TABLE 4

Use of column method for enantiomeric resolution of (±)-bisfuran alcohol.

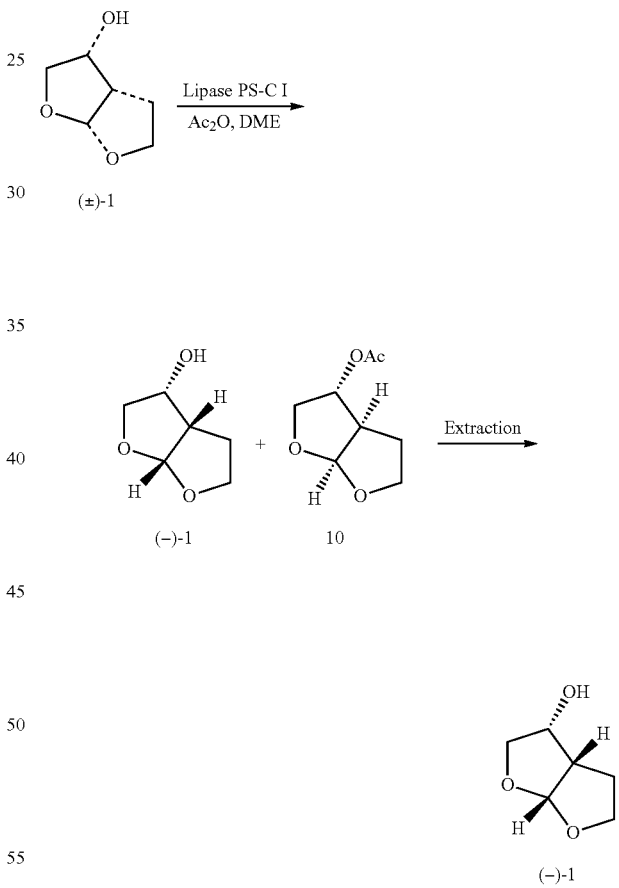

| En-try | Lipase Activ-ity (U/g) | Amt of Lipase (g) | Flow Rate (mL/min) | Resi-dence Time (min) | Total Time (hrs) | Con-version* (ROAc to ROH) (10:1) | Optical Purity (% ee) | Yield (%) |
|---|---|---|---|---|---|---|---|---|
| 1 | 1925 | 18.6 | 17 | 1.8 | 10.5 | 1.5:1.0 | 97.2 | 32 |
| 2 | 1925 | 22.7 | 164 | 0.52 | 19.0 | NA | 98.2 | 42 |
| 3 | 1925 | 275.6 | 2000 | 0.8 | 14.5 | 1.2:1.0 | 97.2 | 33 |

Scheme 1: Process used to prepare bisfuran carbonates from bisfuran alcohols, using the novel process for synthesis of bisfuran alcohols.
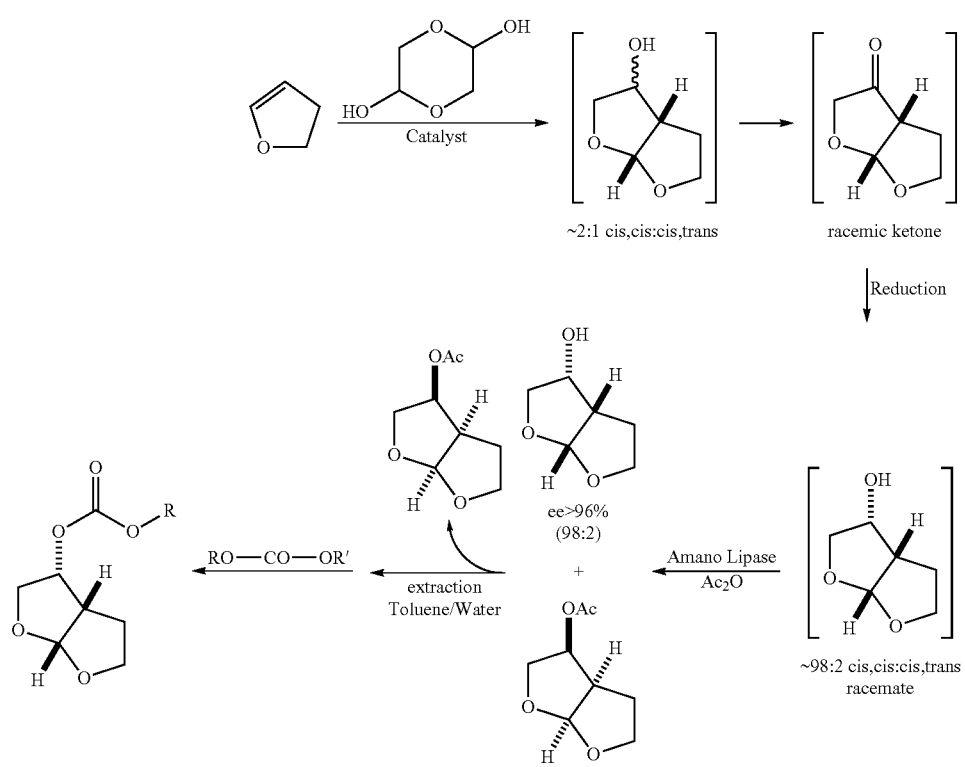
Scheme 2: Amination of chlorohydrins to BOC(OBn)Tyrosine.
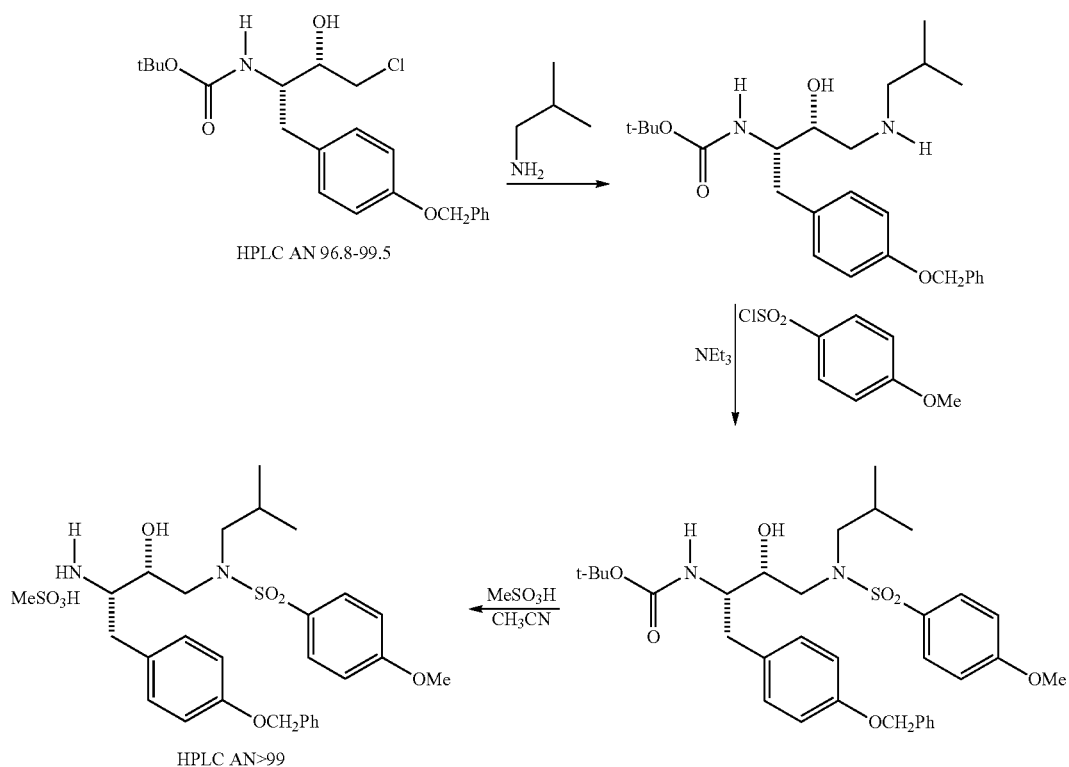

Scheme 3: Reaction of the product obtained in Scheme 2 with a bisfuran carbonate obtained as described in Scheme 1.
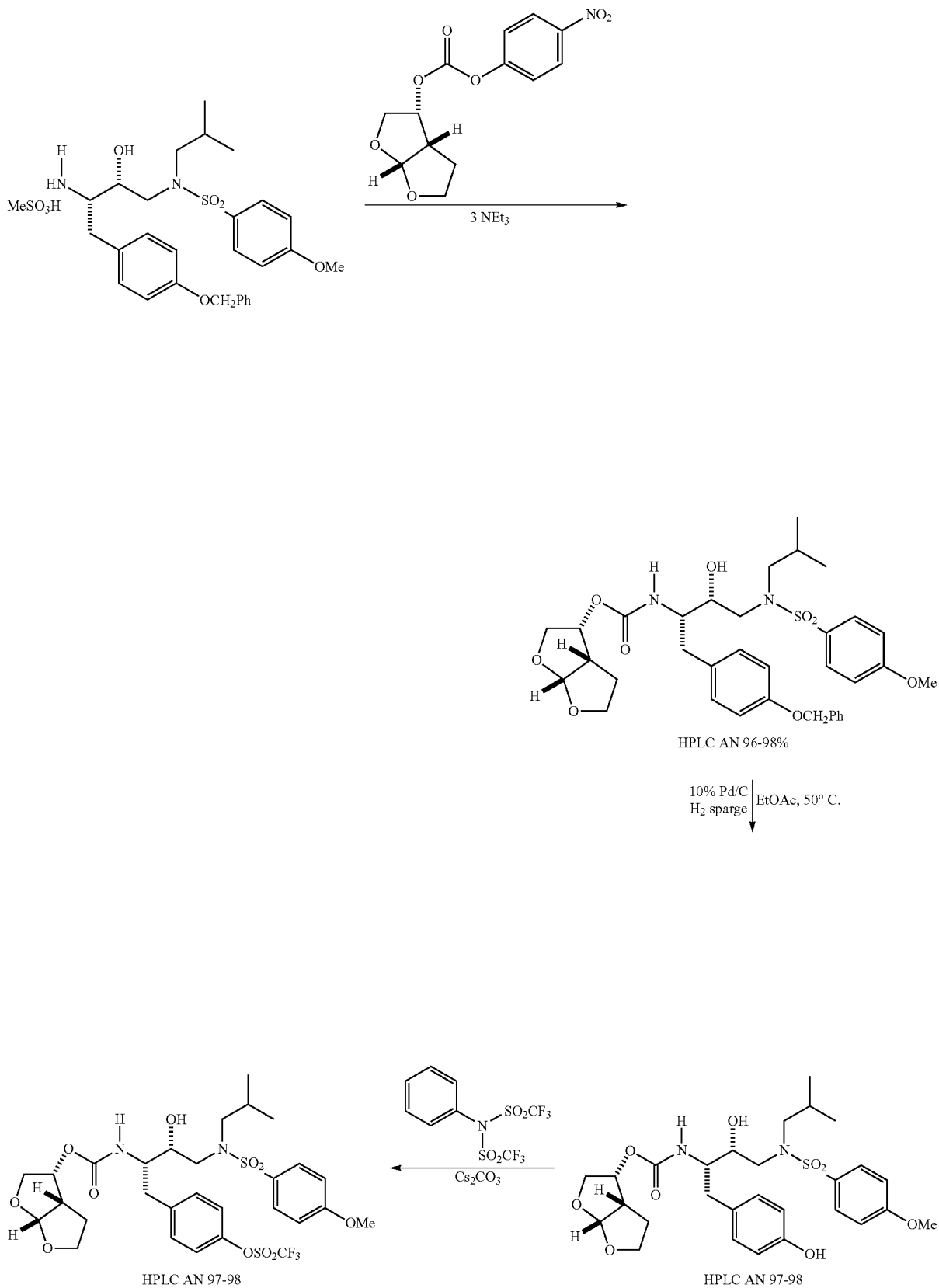

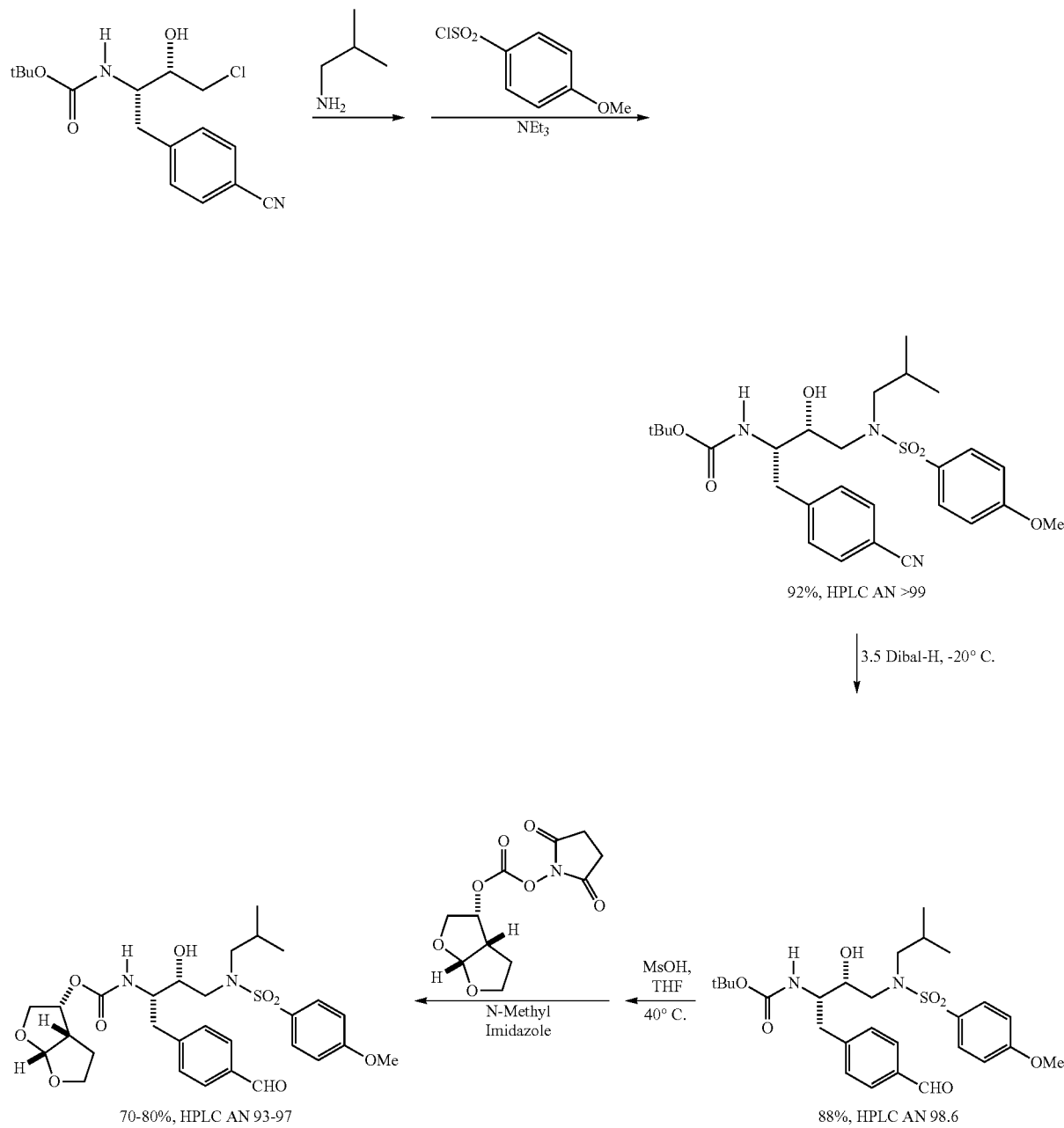
Scheme 4.
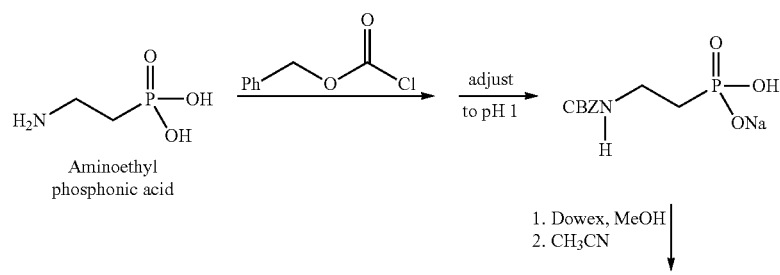
Scheme 5.

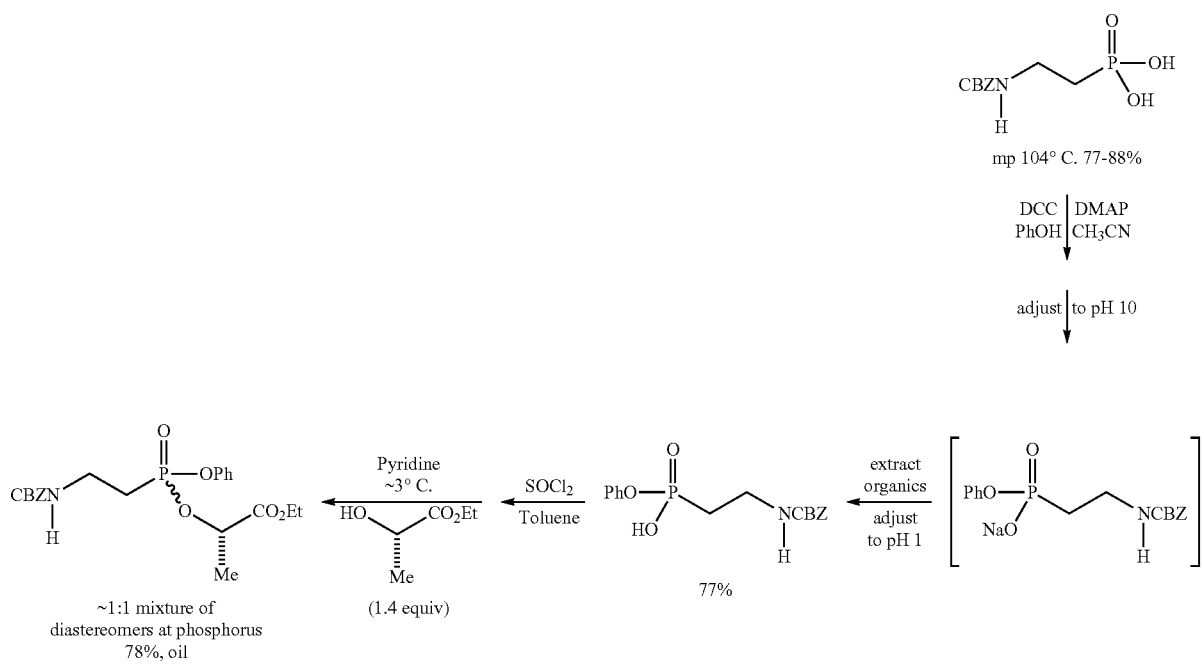
Yamanuchi, K. et al, *J. Org. Chem.*, 1984, 49, 1158; Chapman, H. et al; *Nucl. Nucleotid. Nucleic Acids*, 2001, 20, 621
Scheme 6.
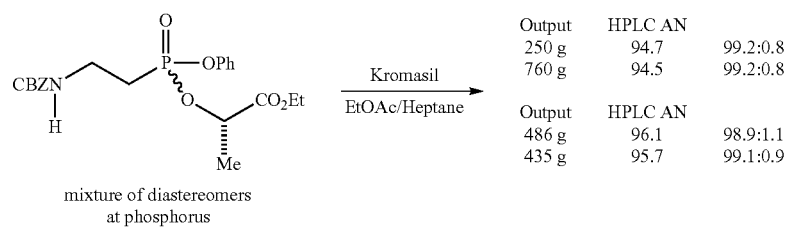
Scheme 7.
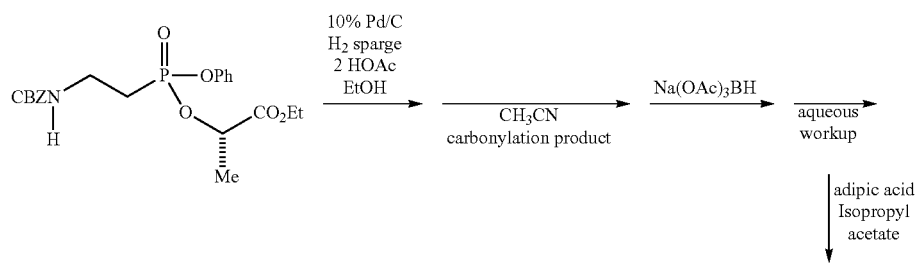

-continued

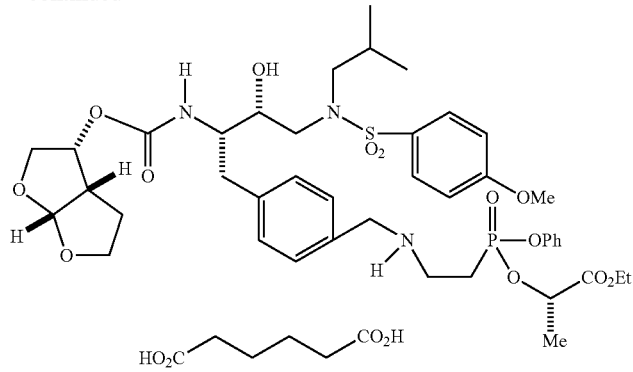

The invention will now be illustrated by the following non-limiting Examples.

Scheme 8.
Kinetic lipase-induced hydrolysis of bisfuran acetate.

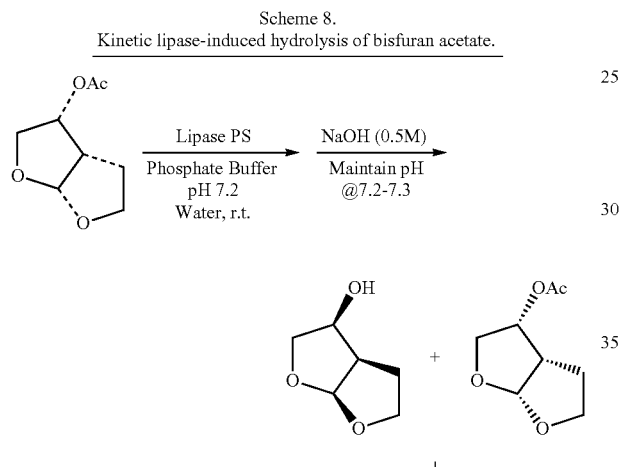

Yield: 47%; 80%ee
(90:10 (-) to (+) ratio)

EXAMPLES

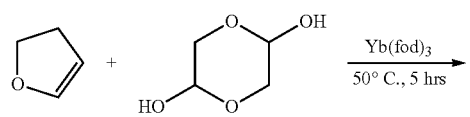

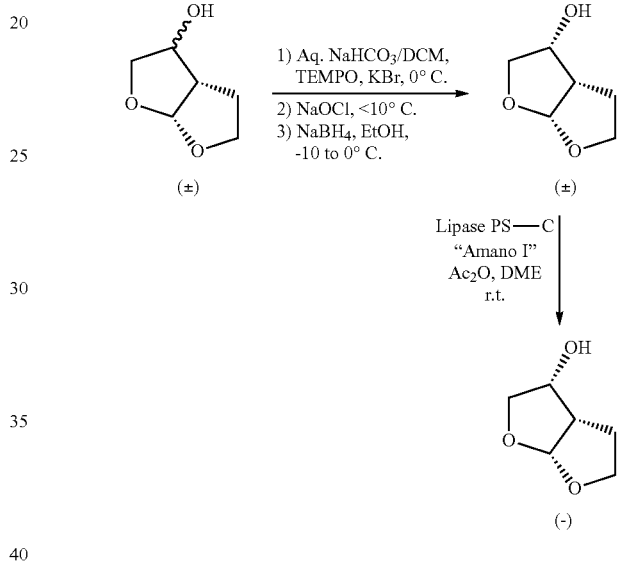

Preparation of,
(3R,3aS,6aR)Hexahydrofuro[2,3-b]furan-3-ol, (1)

To a reaction vessel, charge glycolaldehyde dimer (4.45 kg), Yb(fod)$_3$ catalyst (0.29 kg) and dihydrofuran (20.5 kg). Agitate contents to mix and heat to 50° C. for ~5 hours. Concentrate reaction content to a crude oil, dissolve in saturated aqueous NaHCO$_3$ solution (60 kg), and wash with dichloromethane (6 kg). Charge dichloromethane (58 kg), KBr (0.89 kg), TEMPO (0.116 kg) to the aqueous layer and cool the mixture to 0° C. Slowly add to this mixture with sodium hypochlorite (NaOCl, ~11% Cl, 55 kg). Upon completion of reaction, allow the organic and aqueous layers to separate. Wash the aqueous layer with dichloromethane (29 kg). Combine the organic layers and wash with water, 10% HCl with KI, and 10% sodium thiosulfate. Dry the organic layer over sodium sulfate, filter the solids, and cool the filtrate to below 0° C. Add a solution of sodium borohydride (0.36 kg) in ethanol (7.1 kg) while maintaining reaction content temperature below 0° C. Upon completion of reaction, add acetic acid (1.4 kg) and water (13.4 kg) to quench. Concentrate mixture by vacuum distillation. To the resulting crude oil/semi-solid mixture, add ethyl acetate (31 kg). Dry organic layer over sodium sulfate, filter solids, and concentrate via vacuum distillation to isolate (±)-1 as an oil. Enzymatic Resolution. Charge ethylene glycol dimethyl ether (DME, 14.7 kg) and acetic anhydride (4.6 kg) to the crude product oil. Circulate this solution through a column packed with a mixture of Lipase PS-C "Amano I" (0.36 kg) and sand (6 kg). Upon completion of the enantiomeric resolution, concentrate the solution via vacuum distillation. Add water (18 kg) to dissolve the product and wash the solution with dichloromethane (28 kg). Concentrate the product containing aqueous layer via vacuum distillation. Dissolve the resulting oil in ethyl acetate (16 kg) and dry over sodium sulfate. Additional product can be isolated by back extracting the dichloromethane layer with water several times. Concentrate the combined water layers via vacuum distillation. Dissolve the resulting oil in ethyl acetate, dry over sodium sulfate, and filter solids. Concentrate the combined ethyl acetate layers via vacuum distillation to afford the product, (3R,3αS,6αR) hexahydrofuro[2,3-b]furan-3-ol, (−)-1, as an oil (1.6 kg, 97% ee, 33% yield) contaminated with a approximately 15 wt % of the corresponding acetate. Analytical data: $^1$H NMR (DMSO-d6, 300 MHz) δ 5.52 (dd, 1H), 4.25-4.15 (m, 1H), 3.85-3.75 (m, 2H), 3.7-3.6 (m, 1H), 3.3 (t, 1H), 2.75-2.65 (m, 1H), 2.23-2.13 (m, 1H), 1.75-1.6 (1H).

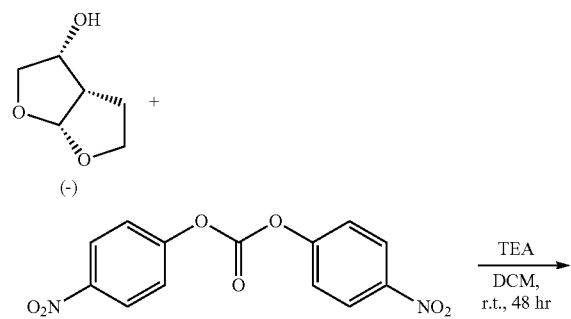

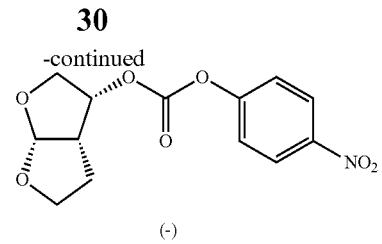

(-)

Preparation of (3R,3aS,6aR)-Hexahydrofuro[2,3-b]furan-3-yl 4-Nitrophenyl Carbonate)

Charge to a reaction vessel with bis(4-nitrophenyl)carbonate (2.85 kg) and dichloromethane (33.4 kg). Add to this solution with (3R,3aS,6aR)-hexahydrofuro[2,3-b]furan-3-ol, (−)-1 (1.2 kg, 98.5% ee, contaminated with ~36% acetate) dissolved in dichloromethane (6.7 kg). Charge triethylamine (1.6 kg) and agitate the resulting reaction contents at 20-25° C. Upon completion of reaction, wash the contents with water (16.8 kg). Separate the layers and concentrate the dichloromethane layer via vacuum distillation. Dissolve the product containing oil in ethyl acetate (21.2 kg) and sequentially wash with water, aqueous potassium carbonate solution and brine. Dry the ethyl acetate layer over sodium sulfate, filter solids, and concentrate via vacuum distillation. Dissolve the concentrated product mixture in ethyl acetate (9.3 kg) and heat to 45° C. Charge hexanes (6.7 kg) slowly and cool the final mixture slowly to 0° C. Filter the resulting slurry to isolate 12. Wash the solid cake with a solution of ethyl acetate and hexanes (1:1 v/v, 5.3 kg). Dry the product to constant weight affording 1.5 kg of 12 (55%) as an off-white solid. Additional product may be obtained by concentrating the mother liquor via vacuum distillation and repeating the crystallization procedure. Analytical data: $^1$H NMR (CDCl$_3$, 300 MHz) δ 8.3 (d, 2H), 7.4 (d, 2H), 5.8 (d, 1H) 5.3-5.2 (m, 1H), 4.2-4.1 (m, 1H), 4.1-3.9 (m, 3H), 3.25-3.1 (m, 1H), 2.3-2.1 (m, 1H), 2.1-1.9 (m, 1H); HPLC AN=98.5%.

Procedure for Formula 12, {(2S,3R)-1-(4-Benzyloxy-benzyl)-2-hydroxy-3-[isobutyl-(4-methoxy-benzenesulfonyl)-amino]-propyl}-[3R,3aS,6aR]-carbamic acid hexahydro-furo[2,3-b]furan-3-yl ester

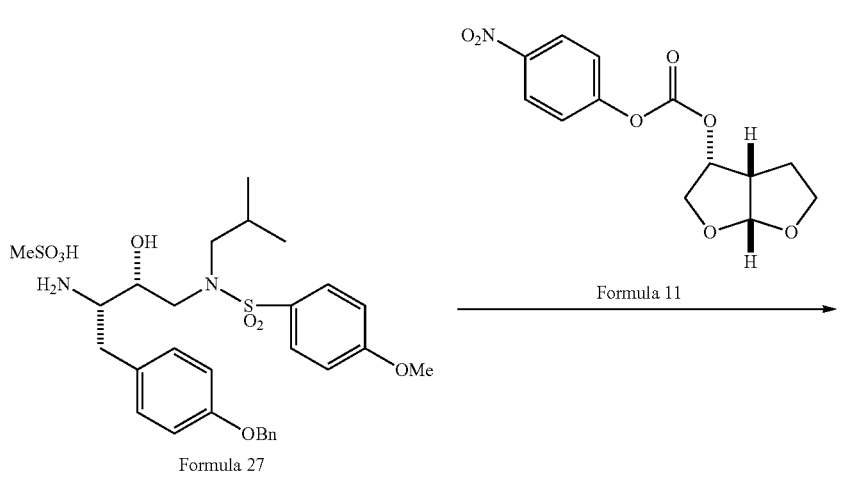

Formula 27

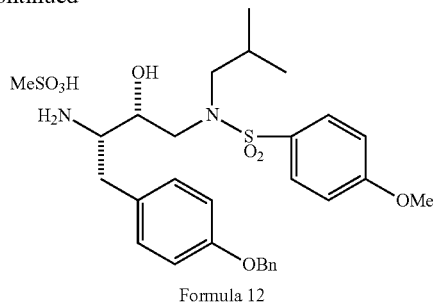

Formula 12

A flask is charged with Formula 27 (1.3 Kg), followed by Formula 12 (0.65 Kg) and ethyl acetate (7.2 Kg) and agitated and triethylamine (0.65 Kg) and dimethylaminopyridine (24 g) added and agitated at ambient temperature for several hours. The reaction mixture is washed sequentially with water (8 Kg), aqueous saturated $NaHCO_3$ (8 L) and dilute aqueous HCl (8 L) and brine (8 L). The reaction mixture is charged with activated charcoal (0.13 Kg), stirred for several hours, filtered through celite and rinsed with ethyl acetate. Heptane (6 L) is added, the mixture agitated for several hours and the product collected by filtration, and rinsed with 1:1 EtOAc/Heptane. The product is dried to constant weight affording 1 Kg of Formula 12 (70%) as an off white solid, mp 127.5° C., HPLC purity 98.4. $^1$H NMR (CDCl$_3$) 7.7-7.75 (d, 2H), 7.26-7.48 (m, 5H), 7.12-7.20 (d, 2H), 6.96-7.03 (d, 2H), 6.85-6.94 (d, 2H), 5.65 (d, 1H), 5.3 (broad d, 1H), 5.01 (s, 2H), 4.96-5.06 (broad, 1H), 3.63-3.96 (m, 7H), 3.84 (s, 3H), 2.62-3.20 (m, 7H), 1.8-1.95 (m, 1H), 1.40-1.69 (m, 2H), 0.95 (dd, 6H).

Procedure for Formula 13, {[1S,2R]-2-Hydroxy-1-(4-hydroxy-benzyl)-3-[N-isobutyl-(N-4-methoxy-benzenesulfonyl)-amino]-propyl}-carbamic acid hexahydro-[3R,3aS,6aR]-furo[2,3-b]furan-3-yl ester A flask is charged with Formula 12 (1 Kg) and flushed with nitrogen. Palladium on activated carbon, 10 wt %, wet, (0.2 Kg) is added, the flask flushed with nitrogen and ethyl acetate (10 L) added and the mixture is heated to 50° C. and hydrogen is sparged into reaction mixture for 2.5 h until reaction is complete. The mixture is sparged with nitrogen and then filtered through celite under nitrogen and then rinsed with ethyl acetate. The filtrate is concentrated to 2.5 L and heptane (7.5 L) added to the warm solution. The resultant slurry is cooled in an ice bath, collected and washed with n-neptane and dried to constant weight affording Formula 13 as a solid, 0.82 Kg, mp: two endotherms at 98.2 and 133.8° C., HPLC purity 97.4%. $^1$H NMR (CDCl$_3$) 7.61-7.75 (d, 2H), 7.01-7.10 (m, 2H), 6.91-6.99 (d, 2H), 6.63-6.79 (d, 2H), 5.62 (d, 2H), 5.51 (broad s, 1H), 4.96-5.09 (d, 2H), 3.81 (s, 3H), 3.59-3.98 (m, 6H), 2.62-3.18 (m, 7H), 1.42-1.91 (m, 3H), 0.78-0.95 (dd, 6H).

Procedure for Formula 14, Trifluoro-methane-sulfonic acid 4-(2S,3R)-{2-([2R,3S]-hexahydro-furo[2,3-b]furan-(3R)-3-yloxycarbonylamino)-3-hydroxy-4-[N-isobutyl-(N-4-methoxybenzenesulfonyl)-amino]-butyl}-phenyl ester

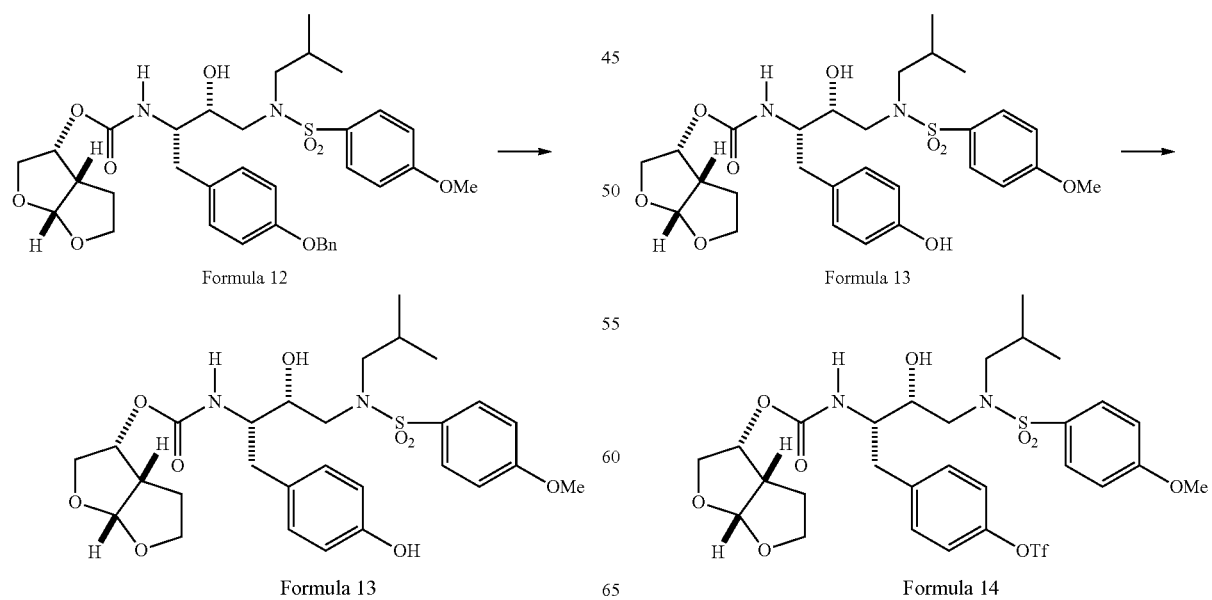

Formula 12

Formula 13

Formula 13

Formula 14

Formula 13 (0.82 Kg) and dichloromethane (8 Kg) were charged into a flask, and gently warmed to dissolve the Formula 13. A separate flask was charged with N-phenyltriflimide (0.61 Kg) and dichloromethane (2.6 Kg) and gently warmed to obtain a solution. A solution of triflating agent was transferred into the solution containing Formula 13 and cesium carbonate (0.55 Kg) was added and stirring continued at ambient temperature for several hours until reaction was complete. Water (4 Kg) was added, the layers separated, the aqueous back extracted with dichloromethane and the combined organic layers dried over anhydrous sodium sulfate. The solution was filtered and concentrated to a small volume and diluted sequentially with methyl tert butyl ether (7 L) and heptane (16 L) and stirred at ambient temperature to obtain a solid which was collected and dried to constant weight to provide Formula 14 as a solid, 0.68 Kg, mp 133.7° C., $^{19}$F NMR (CDCl$_3$) −73.5 ppm, HPLC purity 97.2%. $^1$H NMR (CDCl$_3$) 7.70-7.78 (d, 2H), 7.29-7.38 (d, 2H), 7.16-7.23 (d, 2H), 6.96-7.06 (d, 2H), 5.67 (d, 1H), 4.95-5.04 (m, 2H), 3.87 (s, 3H), 3.64-4.01 (m, 7H), 2.78-3.21 (m, 7H), 1.51-1.90 (m, 3H), 0.87-0.97 (dd, 6H).

Procedure for Formula 15, {(1S,2R)-[1-(4-Formyl-benzyl)]2R)-2-hydroxy-3-[N-isobutyl-(N-4-methoxy-benzenesulfonyl)-amino]-propyl}-carbamic acid [3R,3aS,6aR]-hexahydrofuro[2,3-b]furan-3-yl ester

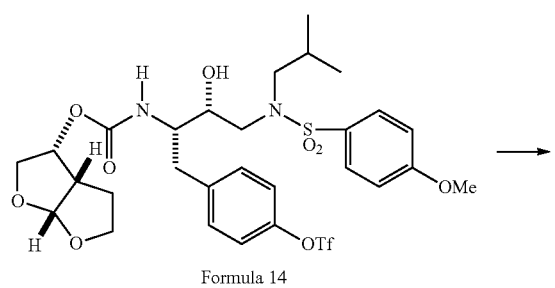
Formula 14

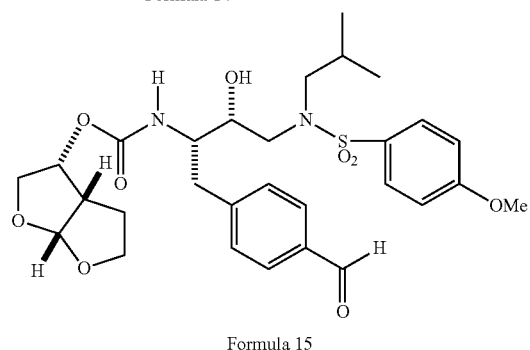
Formula 15

A flask is charged with Formula 14 (0.15 Kg) followed by Pd(OAc)$_2$ (0.06 Kg), dppp. (0.1 Kg), dimethylformamide (1.9 Kg) and sequentially evacuated by vacuum and purged with nitrogen several times and then heated under nitrogen to an internal temperature of 60 to 65° C. and lithium chloride (3 g) is added. The mixture is heated at 65-70° C. and the mixture is sparged with carbon monoxide for 30 minutes. Triethylamine (86 g) is charged to the solution, followed by slow addition of triethylsilane (0.05 Kg). The reaction is maintained at 65-70° C. under a CO atmosphere until the reaction is complete. The reaction mixture is cooled to ambient temperature, diluted with ethyl acetate (1.8 Kg) and washed with water (4 Kg). The ethyl acetate is back extracted with water (1 Kg) and the combined water layers back extracted with ethyl acetate (0.5 Kg). The combined ethyl acetate extracts are washed with water several times and the ethyl acetate filtered through celite, diluted with acetonitrile (0.2 Kg). HF (48% in water, 0.23 Kg) and saturated NaHCO$_3$ (3 Kg) are added, the reaction mixture is separated and the aqueous layer discarded. The organic layer is dried over anhydrous sodium sulfate, filtered and the filtrate heated to a temperature of 50-55° C., treated with trimercaptotriazine (23 g) for several minutes, activated carbon (10 g) added, the mixture heatet at 50-55° C. for at least 30 minutes, cooled to ambient temperature and filtered through a pad of celite. The filtrate is washed with saturated NaHCO$_3$ (0.7 Kg), separated, dried over anhydrous sodium sulfate, filtered, and concentrated and the residue purified by silica gel column chromatography eluting with a mixture of ethyl acetate and heptane. The fractions containing desired Formula 15 are collected and concentrated to afford a white solid which is recrystallized by dissolving in ethylene glycol dimethyl ether at elevated temperature and slow addition of heptane followed by cooling to ambient temperature. Collection of the solid by filtration, rinsing with heptane and drying to constant weight provides Formula 15 as a white solid, 72%, 0.125 Kg, mp 140.2° C., HPLC purity 98.3%. $^1$H NMR (CDCl$_3$) 9.98 (s, 1H), 7.80-7.85 (d, 2H), 7.67-7.76 (d, 2H), 7.39-7.45 (d, 2H), 6.95-7.04 (d, 2H), 5.65 (d, 1H), 4.96-5.12 (m, 2H), 3.85 (s, 3H), 3.64-4.02 (m, 7H), 2.75-3.21 (m, 7H), 1.72-1.89 (m, 1H), 1.42-1.70 (m, 2H), 0.84-0.98, dd, 6H).

Procedure for Formula 16, 2-(N-benzyloxycarbamoyl)-aminoethylphosphonic acid

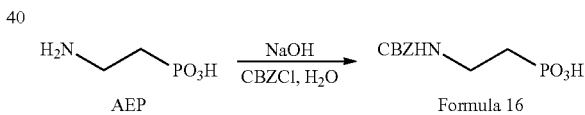

A flask is charged with deionized water (9 Kg), inerted, agitated and charged with sodium hydroxide (2.7 Kg) in portions to maintain the temperature below 35° C.

Aminoethyl phosphonic acid (AEP, 3 Kg) is charged into the flask in portions. Benzyl chloroformate (5.6 Kg) is added in several portions controlling the temperature at approximately between 40° C. The mixture is allowed to react at ambient temperature for several hours until reaction is complete. The mixture is extracted twice with ethyl acetate (16 Kg portions). The aqueous layer is acidified with concentrated HCl to pH 1.3 and aged for several hours. The solid is collected and washed with acetonitrile (2.3 Kg). The solid and methanol (9.6 Kg) is then charged to a flask and treated with Dowex resin (8.7 Kg) that has been prewashed with water and methanol. The mixture is stirred at ambient temperature for 1 h, filtered and rinsed with methanol (3 Kg). The filtrate is concentrated to thick oil, diluted with acetonitrile and azeotroped repeatedly with acetonitrile until residual methanol is removed. The solution is then diluted with acetonitrile, heated to attain a solution, filtered and allowed to cool gradually to ice bath temperature.

The solid is collected and dried to constant weight affording Formula 16 (CBZ-AEP) 4.8 Kg, 77%, mp 107° C., $^{31}$P NMR (D$_2$O) 26.6 ppm. $^1$H NMR (D$_2$O) 7.2-7.36 (broad s, 5H), 4.95 (broad s, 2H), 3.16-3.30 (m, 2H), 1.78-1.94 (m, 2H).

Procedure for Formula 17, Phenyl-2-(N-benzyloxycarbamoyl)-aminoethylphosphonate

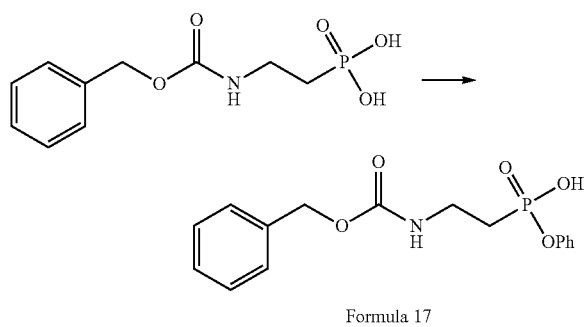

Formula 17

CBZ-AEP (2.5 Kg) and acetonitrile (3.1 Kg) were stirred and heated to 60-65° C. In a separate flask, phenol (4.5 Kg) and acetonitrile (3.5 Kg) were warmed to afford a solution and this solution was charged to the CBZ-AEP mixture and stirred until a solution was obtained. To this solution was charged a slurry of 4-dimethylaminopyridine (DMAP, 1.4 Kg) in acetonitrile (3.1 Kg). In a separate flask was charged acetonitrile (0.8 Kg) and dicyclohexylcarbodiimide (3 Kg) was charged. This DCC solution was added to the warm AEP solution. As soon as the addition was complete, the reaction mixture was refluxed for several hours until the reaction was complete. The reaction mixture was cooled to ambient temperature, filtered and the filtrate concentrated and diluted with water (20 L) and aqueous NaOH. The solution was extracted twice with ethyl acetate (13.5 L). The aqueous phase was acidified to pH of 1.0 by addition of 6M HCl, the resultant solid collected and reslurried with water (19 L) and collected again, and dried to constant weight to provide Formula 17 as a white solid, 2.47 Kg, mp 124° C., HPLC purity 99.2%, $^{31}$P NMR (CDCl$_3$) 29.8 ppm (~90%) and 28.6 ppm (~10%) due to rotamers of the carbamate functional group. $^1$H NMR (CDCl$_3$) 7.05-7.40 (m, 10H), 5.10 (broad s, 2H), 3.41-3.59 (m, 2H), 2.01-2.20 (m, 2H).

Procedure for formula 18, Phenyl, (ethyl(S)-2-propionyl)-2-(N-benzyloxycarbamoyl)-aminoethylphosphonate

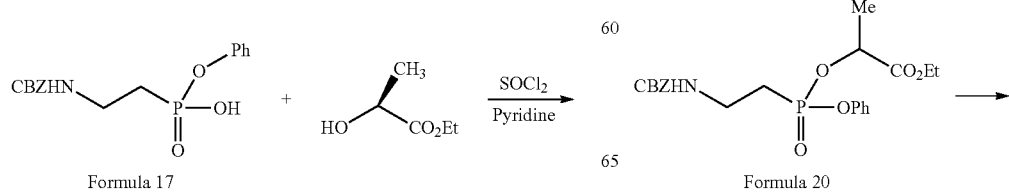

Formula 17

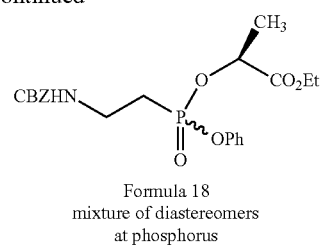

Formula 18
mixture of diastereomers
at phosphorus

Formula 17 (4.8 kg) was charged to the reactor along with toluene (24 kg) and DMF (4 g). The mixture was warmed to 70° C. SOCl$_2$ was added over time while maintaining 67-72° C. internal contents temperature, and the reaction agitated at 75° C. until the reaction was complete. The solution was cooled to 45° C. and concentrated under vacuum to approx. half volume. In a separate reactor a dry solution of (S)-ethyl lactate (1.9 kg), toluene (15 kg), and pyridine (1.5 kg) was prepared and cooled to −1° C. The chloridate solution was added slowly while maintaining an internal temperature of −3 to 3° C. and then the resulting solution was warmed to 20° C. and agitated until the reaction was complete. The reaction was added to a solution of 10% aq. citric acid (10 kg), the layers separated and the organic layer washed with 10% aq. NaH$_2$PO$_4$ (10 kg). The organic layer was dried over anhydrous sodium sulfate (5 kg), concentrated and evaporated from ethyl acetate (4 kg) to a viscous oil which is purified by passing through silica gel plug (9.2 kg) eluting with a mixture of ethyl acetate and heptane. The fractions containing Formula 17 were combined and concentrated to afford an oil. The solvent was exchanged by evaporating twice with acetonitrile (2×3 kg) to afford an thick liquid (4.7 kg, 80%) with HPLC purity 98% as a mixture of two diastereomers (corrected for benzyl chloride).

The mixture of isomers was separated on Chromasil silica gel, eluting with a mixture of ethyl acetate and heptane. The desired isomer Formula 20, displayed the following physical data: Oil, $^{31}$P NMR (CDCl$_3$) 26.1 (~90%) and 25.4 (~10%) due to rotamers of the carbamate functional group; $^1$H NMR (CDCl$_3$) 7.24-7.4 (m, 8H), 7.14-7.21 (m, 2H), 5.65 (broad s, 1H), 5.1 (s, 2H), 5.02-5.06 (m, 1H), 4.12-4.17 (q, 2H), 3.52-3.70 (m, 2H), 2.15-2.36 (m, 2H), 1.57 (d, 3H), 1.22 (t, 3H).

Procedure for Formula 19, Phenyl, (ethyl(S)-2-propionyl)-2-amino ethylphosphonate, acetate salt Formula 20

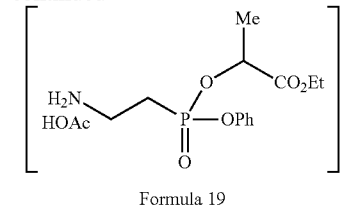

Formula 19

A flask is charged with palladium on activated carbon, 10 wt %, wet (0.28 Kg), acetic acid (0.15 L) and Formula 20 (0.56 Kg) and ethanol (5.6 L) and the flask is sparged with nitrogen for approximately 30 minutes. Hydrogen is sparged into reaction mixture for several hours until the starting material is consumed. The reaction mixture is sparged with nitrogen for 60 minutes and the reaction mixture is filtered through celite and washed with ethyl alcohol (2 L). The filtrate is concentrated at ambient temperature to a small volume, diluted with acetonitrile (5.6 L), concentrated to half volume, and treated with activated carbon (0.3 Kg), filtered through celite and washed with acetonitrile (2.5 L). The filtrate is evaporated at ambient temperature and diluted with acetonitrile and evaporated. This is repeated several times to remove all ethanol and water and the solution finally concentrated to a small volume and stored at 5° C. Evaporation of an aliquot provided yield. Oil, 90%, 0.49 Kg, $^{31}$P NMR (CDCl$_3$) 25.2. The material was used in the next step without further purification.

Procedure for Formula 21, 2-[(2S,3R)-4-[((4-methoxybenzene)sulfonyl)(2-methylpropyl)amino]-3-(hydroxy)butyl]-[[[[(phenoxy)(2-(2R)-propionic acid ethyl ester)oxy]phosphinyl]ethylamino]benzyl]-[carbamic acid-(3R,3aS,6aR)-hexahydrofuro[2,3-b]furan-3-yl ester]hexanedioate salt (1:1)

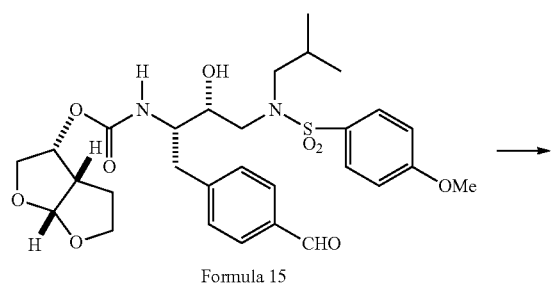

Formula 15

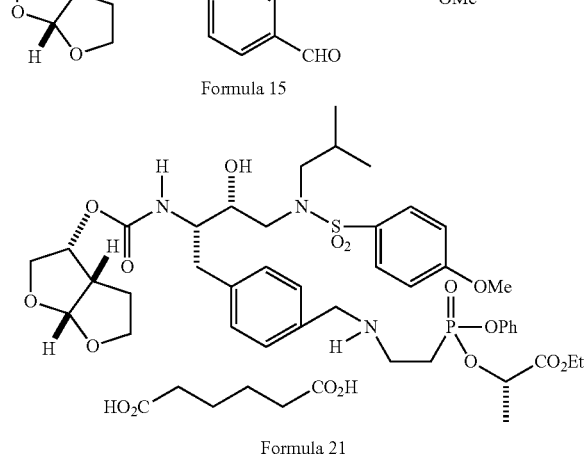

Formula 21

A flask is charged with Formula 15 (0.5 Kg), acetonitrile (1.6 L) and a solution of Formula 19 (0.46 Kg) in acetonitrile (1 L) followed by acetonitrile (2.4 L). The mixture is stirred at ambient temperature several hours. NaBH(OAc)$_3$ (0.27 Kg) is added in portions over time at ambient temperature to maintain at ambient temperature. The reaction mixture is stirred several hours until reaction is complete. Celite (0.24 Kg) is added and the reaction mixture is filtered and washed with acetonitrile and isopropyl acetate. The filtrate is concentrated to a small volume and diluted with isopropyl acetate (12.5 L) and washed sequentially with saturated NaHCO$_3$ three-four times (7.5 L portions), brine (3.8 L), the organic solution dried over sodium sulfate, filtered, concentrated to a small volume, diluted with isopropyl acetate and residual water removed azeotropically. The solution is diluted with acetonitrile, warmed and adipic acid (0.13 Kg) added. The solution is cooled gradually and the solid collected, and rinsed with isopropyl acetate to provide Formula 21 as a solid, 0.69 Kg, 79%, mp 119° C., HPLC purity 95.3%. Spectral data was consistent with that of a reference standard: $^{31}$P NMR (acetone-d6) 27.6; $^{13}$C NMR (acetone-d6) ppm 173.4, 170, 162.6, 155.0, 150.4, 137.9, 137.4, 130.7, 129.3, 129.2, 129.1, 127.6, 124.5, 120.4, 113.9, 108.9, 72.7, 72.6, 70.4, 70.4, 68.6, 60.7, 57.8, 55.6, 54.9, 52.8, 52.3, 45.1, 42.1, 34.9, 32.6, 26.5, 26.5, 25.4, 24.0, 19.2, 18.6, 13.1; $^1$H NMR (acetone d6) ppm 7.80 (d, 2H), 7.38 (t, 2H), 7.29 (d, 2H), 7.28 (d, 2H), 7.26 (d, 2H), 7.21 (t, 1H), 7.12 (d, 2H), 5.53 (d, 1H), 5.04 (dq, 1H), 4.95 (ddd, 1H), 4.14 (q, 2H), 3.92 (s, 3H), 3.89 (m, 1H), 3.88 (dd, 1H), 3.84 (m, 1H), 3.78 (br s, 2H), 3.76 (dd, 1H), 3.63 (dd, 1H), 3.60 (dd, 1H), 3.20 (dd, 1H), 3.06 (dd, 1H), 2.97 (dt, 2H), 2.91 (dd, 1H), 2.85 (m, 1H), 2.70 (dd, 1H), 2.33 (m, 2H), 2.24 (m, 2H), 2.04 (m, 1H), 1.67 (m, 2H), 1.51 (m, 2H), 1.51 (d, 3H), 1.21 (t, 3H), 0.93 (d, 3H), 0.89 (d, 3H); IR (KBr) cm$^{-1}$ 3354, 3424, 3300-2400 (br), 2959, 1755, 1703, 1599, 1497, 1308, 1343, 1152, 991, 950.

Procedure for Formula 21b, 2-[(2S,3R)-4-[((4-methoxybenzene)sulfonyl)(2-methylpropyl)amino]-3-(hydroxy)butyl]-[[[[(phenoxy)(2-(2R)-propionic acid ethyl ester)oxy]phosphinyl]ethylamino]benzyl]-[carbamic acid-(3R,3aS,6aR)-hexahydrofuro[2,3-b]furan-3-yl ester]butanedioate salt (1:1)

Prepared by dissolving 7.8 g of the free base Formula 29 by agitating in hot isopropyl acetate (~200 mL), charging succinic acid (1 equivalent), and after a solution is obtained the solution is gradually cooled to ambient temperature and then cooled in an ice bath for several minutes, the product collected and rinsed with isopropyl acetate and dried to constant weight providing Formula 21b succinate salt, 7.7 g, 86%, HPLC purity 98.6%, mp 106.5° C. $^{13}$C NMR (CDCl$_3$) 129.8, 129.4, 129.2, 124.9, 120.3, 114.1, 109.0, 70.9, 72.7, 71.4, 70.33, 70.28, 69.34, 69.30, 61.3, 56.51, 56.47, 55.3, 54.95, 52.24, 52.22, 51.74, 51.72, 44.93, 42.42, 30.65, 24.84, 24.79, 26.48, 25.42, 19.7, 19.6, 19.24, 13.7. $^1$H NMR (CDCl$_3$) 7.75-7.79 (d, 2H), 7.38-7.43 (d, 2H), 7.33-7.36 (m, 2H), 7.24-7.29 (d, 2H), 7.15-7.20 (t, 1H), 6.98-7.05 (4H), 5.63 (d, 1H), 5.00-5.08 (m, 1H), 5.84-4.92 (m, 1H), 4.09-4.18 (m, 3H), 3.93-3.98 (m, 1H), 3.91 (s, 3H), 3.79-3.92 (m, 4H), 3.66-3.74 (m, 1H), 3.22-3.56 (m, 4H), 2.96-3.02 (m, 2H), 2.51-2.83 (m, 10H), 1.74-1.82 (m, 2H), 1.6 (d, 3H), 1.46-2.01 (3H), 1.21 (t, 3H), 1.83 (d, 3H), 1.63 (d, 3H).

Procedure for Formula 22

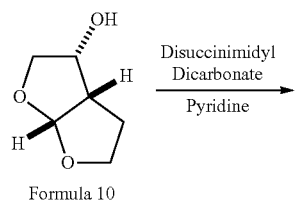

Formula 10

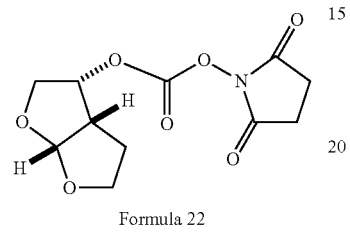

Formula 22

A flask is charged with 14.8 g of disuccidimidylcarbonate, CH$_2$Cl$_2$ (25 mL), 5.0 g of Formula 10 as a solution in CH$_2$Cl$_2$ (20 mL), and pyridine (7.8 mL). The solution is heated at gentle reflux for several hours until reaction completes. Heating is removed and water (35 mL) is added, the mixture agitated several minutes, the layers are separated. The organic phase is washed sequentially with water (35 mL) and brine (30 mL). The organic phase is dried over sodium sulfate, filtered and concentrated. The residue is redissolved in dichloromethane CH$_2$Cl$_2$ (13 mL) with heating and heptane (10 mL) added to the warm solution. The mixture is gradually cooled to approximately 10° C., the solid filtered, rinsed with heptane and dried to constant weight providing ~8.9 g 87.5%.

A flask is charged with crude Formula 22 (106 g), activated carbon (23 g) and toluene (5.7 Kg). After agitation for 2 h the mixture is filtered through celite and the filtrate evaporated to afford 100 g (94.3% recovery) of Formula 22 as an off-white solid. A flask is charged with Formula 22 (12 g) of Formula 22, acetone (24 g) and heated to 52° C. to obtain a solution. Heptane (60 g) is added to the warm solution under agitation. The mixture is cooled over two hours to approximately 10° C., the solid collected, washed the with 3:1 acetone:heptane and dried to constant weight, providing Formula 22, 11.4 g, 95% recovery, as a white solid. $^1$H NMR (CDCl$_3$) 5.75 (d, 1H), 5.21-5.30 (dd, 1H), 3.90-4.16 (m, 4H), 3.07-3.18 (m, 1H), 2.85 (s, 4H), 2.10-2.22 (m, 1H), 1.92-2.06 (m, 1H).

Preparation of Formula 24

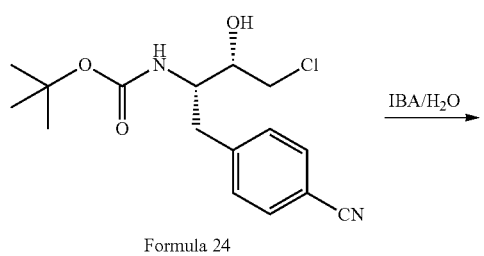

Formula 24

IBA/H$_2$O →

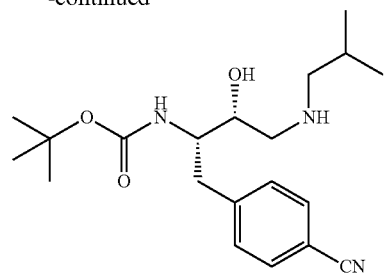

Formula 23

A flask is charged with Formula 24 (10 g), potable water (7.5 g, 13.5 eq.) and isobutylamine (22.08 g, 9.8 eq.), the thick mixture heated to ~60° C., and agitated at this temperature until reaction completed. The reaction mixture is charged with 100 mL potable water over ~30 minutes while maintaining the internal temperature >55° C. The mixture is cooled to 5° C. over 1.5 hours, and held at that temperature for an additional 30 minutes. The slurry is filtered, washed with 20 mL of potable water, and dried to constant weight providing Formula 23, 10.94 g; 98.4%, HPLC purity 97.9%. $^1$H NMR (CDCl$_3$) 7.55-7.62 (d, 2H), 7.32-7.38 (d, 2H), 4.62-4.72 (broad s, 1H), 3.78-3.90 (broad m, 1H), 3.42-3.50 (m, 1H), 3.08-3.16 (dd, 1H), 2.63-2.90 (m, 3H), 2.42 (d, 2H), 1.65-1.81 (m, 1H), 1.35 (s, 9H), 0.93 (d, 6H).

Preparation of Formula 25

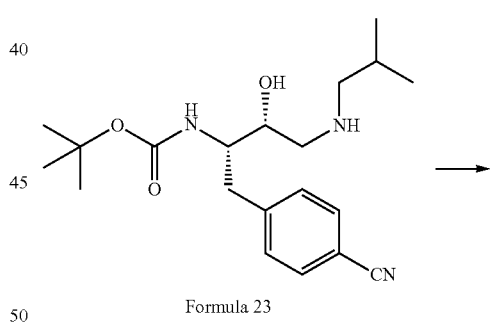

Formula 23

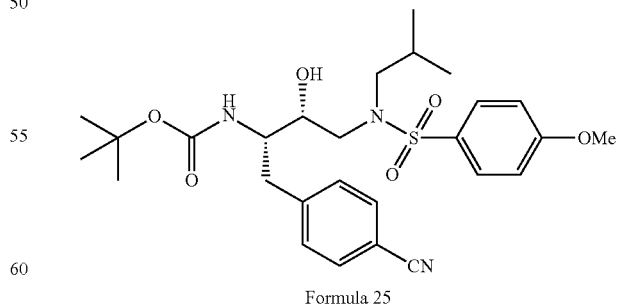

Formula 25

A flask is charged with Formula 23 (10.5 g), dichloromethane (63 mL) and triethylamine (3.1 g, 1.05 eq.) and a solution of 4-methoxyphenylsulfonyl chloride (6.1 g, 1.02 eq.) in dichloromethane (18 mL) added over ~10 minutes, maintaining the internal temperature <25° C. during the addition. Following reaction completion (~2 h at ambient temperature) 1M aqueous HCl (5 mL) is added, agitated for 5 min, and the layers separated. 1 M aqueous NaHCO₃ (5 mL) are added to the organic phase and the mixture agitated for 5 min, the layers separated and the organic phase concentrated to a foam. The crude product is dissolved in 200 mL EtOH at 65° C., water (120 mL) added over ~45 minutes, while maintaining the internal temperature >57° C., and the mixture d, 2H), 7.36-7.43 (d, 2H), 6.96-7.04 (d, 2H), 4.63-4.72 (broad s, 1H), 3.88 (s, 3H), 3.72-3.90 (m, 2H), 3.04-3.18 (m, 3H), 2.79-3.01 (m, 3H), 1.78-1.92 (m, 1H), 1.62 (broad s, 1H), gradually cooled to 10° C. over approximately 4.5 hours. The slurry is filtered and washed with 50 mL of 30% aqueous EtOH, the product dried to constant weight providing 14.5 g, 94%, HPLC purity 99.86%. ¹H NMR (CDCl₃) 7.70-7.76 (d, 2H), 7.55-7.64 (1.35 (s, 9H), 0.85-0.95 (dd, 6H).

Procedure for Formula 26

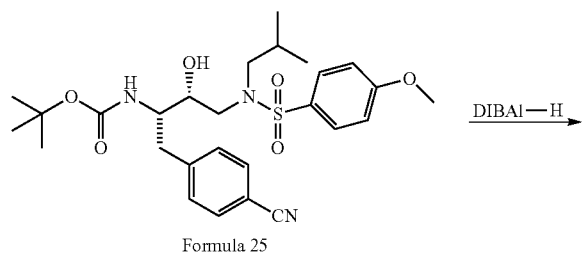

Formula 25

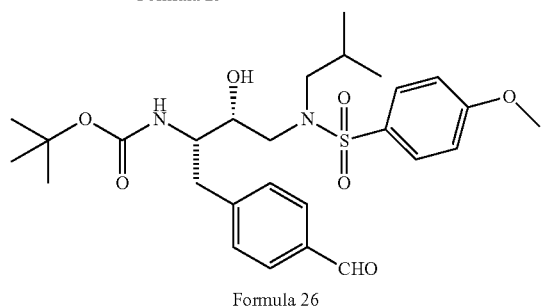

Formula 26

A flask is charged with Formula 25 (35 g), toluene (525 mL), inerted and cooled to −20° C. A solution of 1.5 M DIBAL-H in toluene (154 mL, 1.5 M, 3.5 equiv.) is added gradually, keeping the temperature below −10° C. The reaction is agitated for several hours at this temperature until complete. Methanol (9.3 mL, 3.5 eq.) is charged gradually, followed by THF (88 mL), and the mixture warmed above 0° C. Aqueous citric acid (220 ml of 40% (w/w) of citric acid, 7 eq.) diluted with 130 ml of water) is added over 5 minutes and the mixture then warmed ~60° C. for approximately 1 hour. The mixture is cooled to ambient temperature, the layers separated, and the organic layer added to 175 ml of 1M HCl and 35 ml of water. The separatory funnel is rinsed forward with 105 ml of THF. The resulting mixture is agitated at room temperature for approximately 1 hour, diluted with THF (35 mL), separated, the organic layer combined with 35 ml of 1 M NaHCO₃ and agitated for 30 minutes. The layers were separated, filtered through a layer of anhydrous magnesium sulfate (approximately 2 g) and rinsed with toluene (35 mL). The solution is concentrated and azeotroped with toluene three times to decrease residual THF. The final volume is adjusted to approximately 275 mL and the slurry heated ~65° C. to attain a solution. Heptane (132 mL) is added gradually and the mixture then gradually cooled over 4 h to ambient temperature. The product is filtered, washed with 2:1 toluene: heptane, and dried to constant weight, providing Formula 26, 31 g, 88%, mp 120.5° C., HPLC purity 99.6%. ¹H NMR (CDCl₃) 10.0 s, 1H), 7.80-7.85 (m, 4H), 7.27-7.50 (d, 2H), 7.09-7.10 (d, 2H), 5.99-6.07 (broad d, 1H), 3.91 (s, 3H), 3.78-3.93 (m, 3H), 3.41-3.51 (dd, 1H), 3.24-3.34 (dd, 1H), 2.79-3.05 (m, 5H), 1.29 (s, 9H), 0.87-0.93 (dd, 6H).

Procedure for formula 15, {(1S,2R)-[1-(4-Formyl-benzyl)]-(2R)-2-hydroxy-3-[N-isobutyl-(N-4-methoxy-benzenesulfonyl)-amino]-propyl}-carbamic acid [3R,3aS,6aR]-hexahydrofuro[2,3-b]furan-3-yl ester

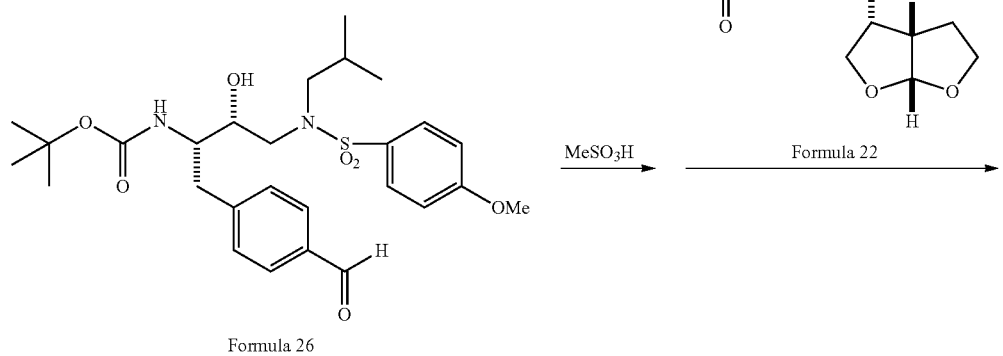

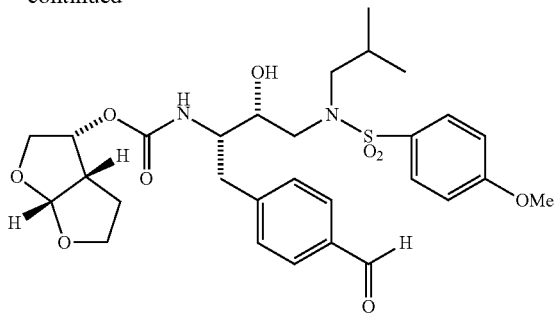

Formula 15

A flask is charged with Formula 26 (2.0 g) and 20 mL THF. Methanesulfonic acid was added drop-wise to the solution. The solution is warmed to 40° C. until de-protection was complete. The solution was cooled to 20° C. and N-methylimidazole (2.39 g) was added to the reactor. Formula 22 (1.52 g) was then charged and the reaction was warmed to 50° C. until the reaction was complete. Ethyl acetate (150 mL) was charged and the solution was sequentially washed with 0.5 M aq. citric acid (20 g), 10% aq. $NaH_2PO_4$ (20 g), sat. $NaHCO_3$ (20 g), and 10% aq. $NaH_2PO_4$ (20 g). The organic layer was dried over anhydrous sodium sulfate (2 g), filtered, and concentrated to a viscous oil which was purified by silica gel column chromatography eluting with a mixture of ethyl acetate and heptane. The fractions containing desired Formula 15 were combined and concentrated to afford a white solid, 95%, 2.13 g, HPLC purity 97%.

Reference has been made to certain embodiments of the invention, examples of which are illustrated in the accompanying description, structures and formulas. While the invention has been described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

What is claimed is:

1. A compound having the formula C:

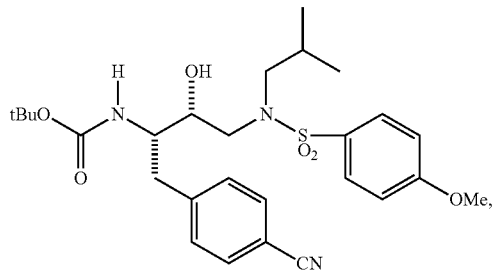

Formula C or a pharmaceutically acceptable salt thereof.

2. A compound having the formula M:

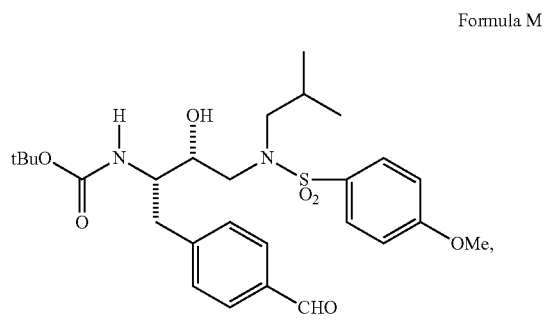 [SMILES: COc1ccc(S(=O)(=O)N(CC(C)C)C[C@@H](O)[C@H](Cc2ccc(C=O)cc2)NC(=O)OC(C)(C)C)cc1]

Formula M or a pharmaceutically acceptable salt thereof.

3. A compound having the formula N:

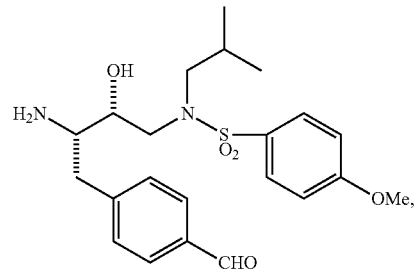

Formula N or a pharmaceutically acceptable salt thereof.

* * * * *